United States Patent
Bixby et al.

(10) Patent No.: US 11,666,323 B1
(45) Date of Patent: Jun. 6, 2023

(54) SOFT ANCHORS HAVING INCREASED ENGAGEMENT BETWEEN DEPLOYMENT SUTURES AND SLEEVE

(71) Applicant: RIVERPOINT MEDICAL, LLC, Portland, OR (US)

(72) Inventors: Elliot Bixby, Gladstone, OR (US); Nathan Daniel Cook, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 174 days.

(21) Appl. No.: 17/407,331

(22) Filed: Aug. 20, 2021

Related U.S. Application Data

(60) Provisional application No. 63/071,278, filed on Aug. 27, 2020.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/042* (2013.01); *A61B 2017/0409* (2013.01); *A61B 2017/0414* (2013.01); *A61B 2017/0464* (2013.01)

(58) Field of Classification Search
CPC .......... A61B 17/0401; A61B 17/06166; A61B 2017/0409; A61B 2017/0414; A61B 2017/0464; A61B 2017/0404; A61B 2017/0406; A61B 2017/0446; A61B 2017/045; A61B 2017/0451; A61B 2017/0454; A61B 2017/0456; A61B 2017/0461; A61B 2017/0462; A61F 2/0811; A61F 2/0817; A61F 2/0847; A61F 2/0876

See application file for complete search history.

(56) References Cited

U.S. PATENT DOCUMENTS

| | | | | |
|---|---|---|---|---|
| 6,010,514 A | * | 1/2000 | Burney | A61B 17/0482 606/144 |
| 6,511,498 B1 | * | 1/2003 | Fumex | A61B 17/0401 606/232 |
| 7,857,830 B2 | * | 12/2010 | Stone | A61B 17/0401 606/232 |

(Continued)

*Primary Examiner* — Shaun L David
*Assistant Examiner* — Zehra Jaffri
(74) *Attorney, Agent, or Firm* — Timothy E. Siegel Patent Law, PLLC; Timothy E. Siegel

(57) ABSTRACT

A soft anchor having a sleeve, being a circular braided suture defining a lumen, and defining a first terminus, having a first terminus opening and a second terminus having a second terminus opening. Also, a deployment suture is engaged to the sleeve by extending into the lumen through a first broach point, then out of the sleeve through the first terminus opening, then into the sleeve through a second broach point, on the bottom-side, and then out of the lumen though a third broach point, then into the lumen through the second terminus opening and out of the suture though a fourth broach point, thereby creating a first lateral trap, between the first broach point and the first terminus opening, a second lateral trap, between the second terminal opening and the fourth broach point, and a central trap, between the second and third broach points.

22 Claims, 2 Drawing Sheets

(56) References Cited

U.S. PATENT DOCUMENTS

| | | | |
|---|---|---|---|
| 7,959,650 B2* | 6/2011 | Kaiser | A61B 17/06166 606/232 |
| 8,298,262 B2* | 10/2012 | Stone | A61B 17/0401 606/232 |
| 9,486,202 B2* | 11/2016 | Ferguson | A61B 17/0485 |
| 9,492,158 B2* | 11/2016 | Stone | A61F 2/0811 |
| 9,872,677 B2* | 1/2018 | Anderson | D01D 10/02 |
| 10,307,154 B2* | 6/2019 | Michalik | A61B 17/0401 |
| 10,966,705 B2* | 4/2021 | Rodriguez | A61B 17/06166 |
| 11,207,062 B2* | 12/2021 | Ferguson | A61B 17/0401 |
| 11,357,497 B1* | 6/2022 | Anakwenze | A61F 2/0811 |
| 11,523,813 B1* | 12/2022 | Ferguson | A61B 17/0485 |
| 2007/0185532 A1* | 8/2007 | Stone | A61B 17/0482 606/232 |
| 2008/0140093 A1* | 6/2008 | Stone | A61B 17/0401 606/228 |
| 2011/0264141 A1* | 10/2011 | Denham | A61B 17/0401 606/232 |
| 2012/0197271 A1* | 8/2012 | Astorino | A61B 17/0469 606/232 |
| 2013/0110165 A1* | 5/2013 | Burkhart | A61B 17/0401 606/232 |
| 2013/0131722 A1* | 5/2013 | Marchand | A61B 17/0401 606/232 |
| 2013/0296934 A1* | 11/2013 | Sengun | A61B 17/0401 606/232 |
| 2014/0052178 A1* | 2/2014 | Dooney, Jr. | A61B 17/0401 606/232 |
| 2015/0142050 A1* | 5/2015 | Ferguson | A61B 17/0401 606/228 |
| 2015/0173754 A1* | 6/2015 | Norton | A61B 17/0401 606/228 |
| 2015/0335327 A1* | 11/2015 | Ferguson | A61B 17/0401 606/228 |
| 2016/0074030 A1* | 3/2016 | Dreyfuss | A61F 2/0811 606/232 |
| 2017/0020655 A1* | 1/2017 | Dreyfuss | A61F 2/0811 |
| 2017/0181739 A1* | 6/2017 | Breslich | A61B 17/0401 |
| 2017/0281327 A1* | 10/2017 | Kaplan | A61F 2/0811 |
| 2017/0290578 A1* | 10/2017 | Thal | A61B 17/0401 |
| 2018/0132841 A1* | 5/2018 | Dreyfuss | A61B 17/0401 |
| 2018/0338756 A1* | 11/2018 | Black | A61B 17/0401 |
| 2019/0015092 A1* | 1/2019 | Bosworth | A61B 17/0401 |
| 2019/0022271 A1* | 1/2019 | Ferguson | A61B 17/06166 |
| 2020/0360009 A1* | 11/2020 | Lombardo | A61B 17/0401 |
| 2020/0405282 A1* | 12/2020 | Miller | A61B 17/0401 |
| 2021/0259676 A1* | 8/2021 | Anderson | A61B 17/06066 |
| 2021/0353280 A1* | 11/2021 | Black | A61B 17/0401 |
| 2023/0056585 A1* | 2/2023 | Goncalves | A61B 17/0401 |

* cited by examiner

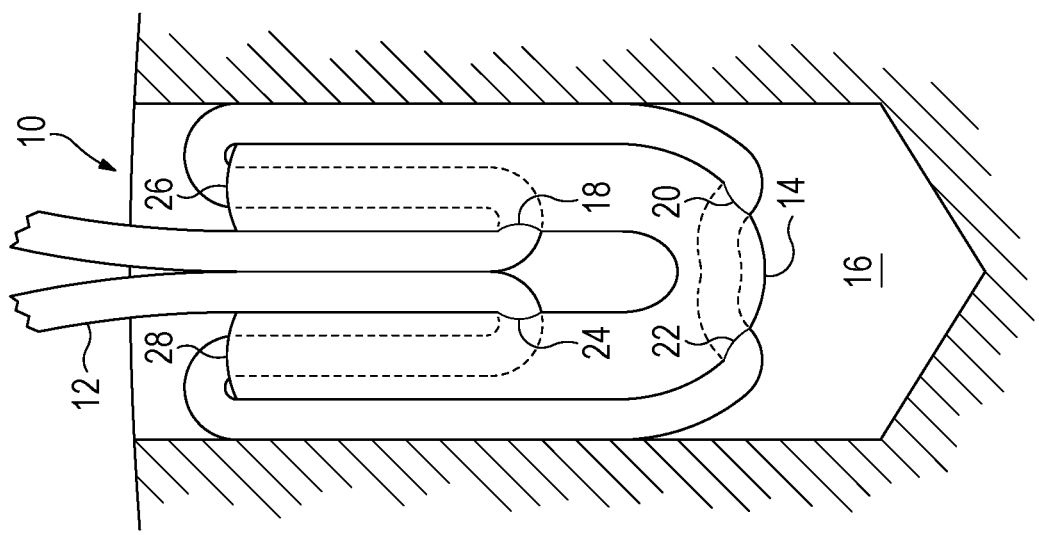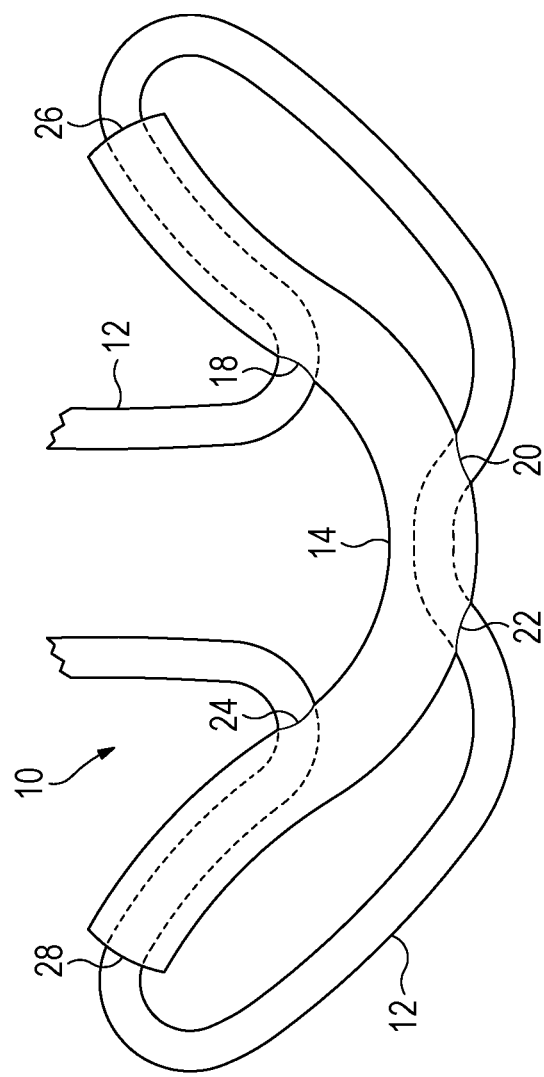

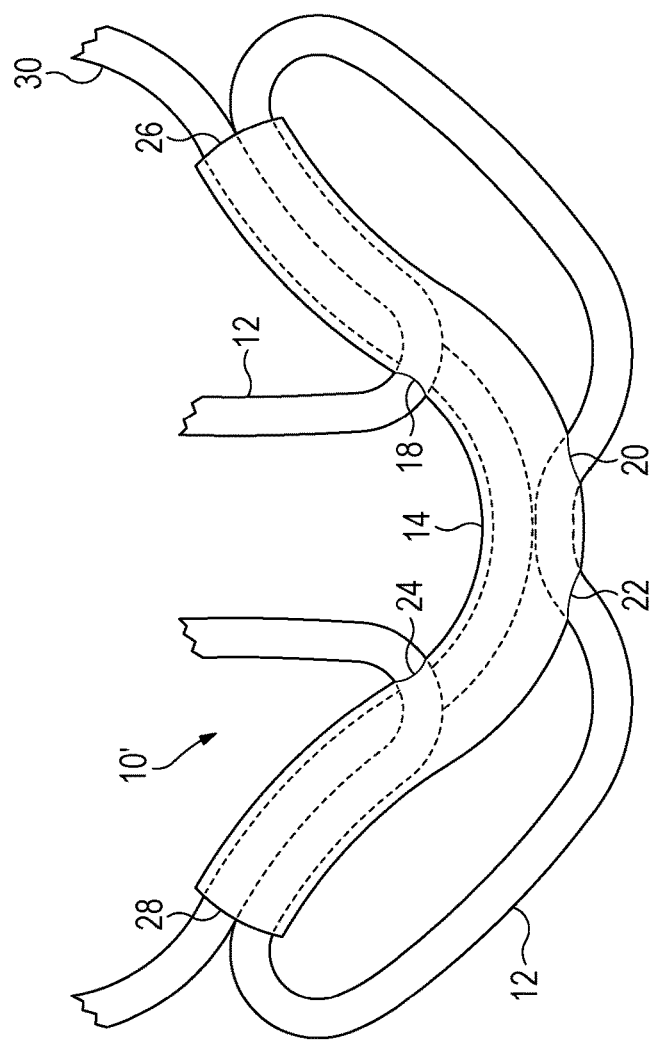
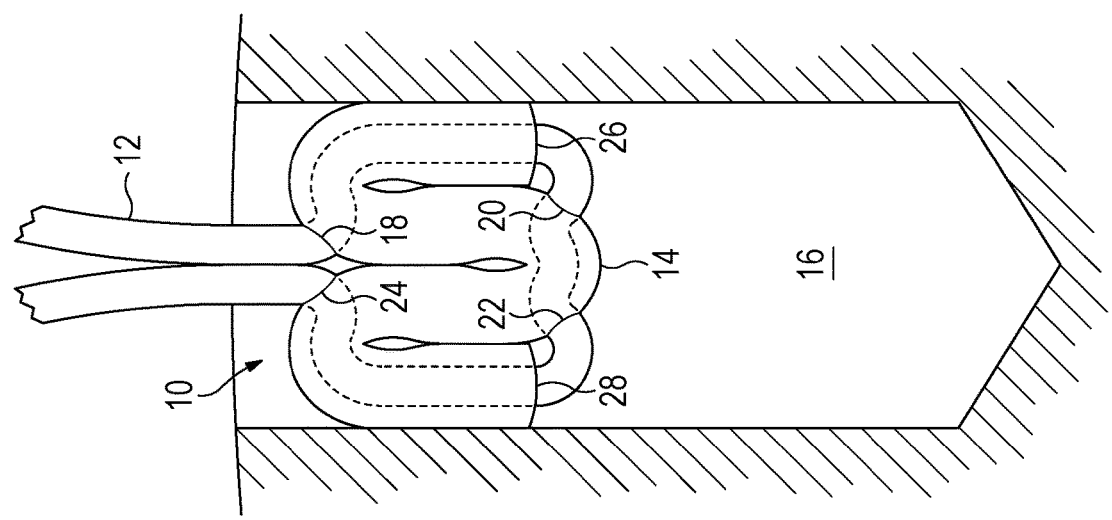

SOFT ANCHORS HAVING INCREASED ENGAGEMENT BETWEEN DEPLOYMENT SUTURES AND SLEEVE

RELATED APPLICATIONS

This application claims benefit of provisional patent application, U.S. Ser. No. 63/071,278, filed Aug. 27, 2020, which is incorporated by reference as if fully set forth herein.

BACKGROUND OF THE INVENTION

There are many soft, all-suture, anchor designs that include a sleeve and a deployment suture that passes through said sleeve and is pulled on to set the anchor. There is a trade-off between anchor size, which dictates the minimum size of the pilot hole that receives the anchor, and the load-bearing capacity of an anchor, which limits an anchor design's possible uses.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a soft anchor having a sleeve, being a circular braided suture defining a lumen, and defining a first terminus, having a first terminus opening into the lumen and a second terminus having a second terminus opening into the lumen. Also, a deployment suture is of a smaller diameter than the sleeve and is engaged to the sleeve by extending into the lumen through a first broach point, then out of the sleeve through the first terminus opening, then into the sleeve through a second broach point, on the bottom-side, and then out of the lumen though a third broach point, then into the lumen through the second terminus opening and out of the suture though a fourth broach point, thereby creating a first lateral trap, between the first broach point and the first terminus opening, a second lateral trap, between the second terminal opening and the fourth broach point, and a central trap, between the second and third broach points.

In a second separate aspect, the present invention may take the form of a method of anchoring a suture to pilot hole in bone, which makes use of a soft anchor that includes a sleeve, having being a circular braided suture defining a lumen, and defining a first terminus, having a first terminus opening into the lumen and a second terminus having a second terminus opening into the lumen. Further, a deployment suture, being of a smaller diameter than the sleeve, and being engaged to the sleeve by extending into the lumen through a first broach point, then out of the sleeve through the first terminus opening, then into the sleeve through a second broach point, and then out of the lumen though a third broach point, then into the lumen through the second terminus opening and out of the suture though a fourth broach point, thereby creating a first lateral trap, between the first broach point and the first terminus opening, a second lateral trap, between the second terminal opening and the fourth broach point, and a central trap, between the second and third broach points. In the method an introducer tool sized to push the soft anchor into the pilot hole is used to push the soft anchor into the pilot hole and is removed. Then both ends of the deployment suture are pulled, thereby causing the soft anchor to deform and expand in a transverse dimension so that it is set in the pilot hole.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced drawings. It is intended that the embodiments and figures disclosed herein are to be considered illustrative rather than restrictive.

FIG. 1 is a plan view of an embodiment of an all-suture anchor, according to the present invention.

FIG. 2 is a sectional view of the anchor of FIG. 1, inserted into a pilot hole.

FIG. 3 is a sectional view of the anchor inserted into the pilot hole of FIG. 2, with a further step taken of having set the anchor by pulling on deployment suture ends.

FIG. 4 is a plan view of an alternative embodiment of an all-suture anchor.

DETAILED DESCRIPTION AND EMBODIMENTS

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

To assist the description of the scope and its components the coordinate terms [top-side and bottom-side] are used to describe the disclosed embodiments. The terms are used consistently with the description of the exemplary applications and are in reference to a preferred orientation of the anchor relative to a pilot hole, with the anchor top-side being on top (that is closer to the opening of the hole) of the anchor bottom side when the anchor is in the pilot hole, in the preferred orientation.

Referring to FIG. 1, a soft, all-suture anchor 10, includes a deployment suture 12 engaged to a sleeve 14, which is a braided, circular suture, defining a lumen. Anchor 10 has a preferred orientation, relative to the pilot hole 16 (FIG. 2), which defines a top-side and a bottom-side of 10, which coincides with the top and bottom in the drawings. In the production process, the sleeve 14 is broached in a first broach point 18, on the top-side of anchor 10, a second broach point 20, on the bottom-side, a third broach point 22, also on the bottom side, and a fourth broach point 24, on the top-side. Anchor 10 is pushed into the pilot hole 16, using an introducer tool (not shown). The deployment suture 12 is engaged to sleeve 14, entering the lumen of sleeve 14 at the first broach point 18, on the top side of sleeve 14, then exiting at a first terminus opening 26, entering again at the second broach point 20, and then exiting at third broach point 22. Both second and third broach points 20, 22 are on the bottom-side of sleeve 14. Then, deployment suture 12 enters sleeve 14 at a second terminus opening 28, and exits at fourth broach point 24, on the top side of sleeve 14. Accordingly, three traps are present, a first lateral trap between first broach point 18 and first terminus opening 26; a central trap between second and third broach points 20 and 22, respectively; and a third lateral trap between second terminus opening 28 and fourth broach point 24.

To place into use, anchor 10 is pushed into the pilot hole 16, using an introducer tool (not shown). Then deployment suture 12 is pulled, causing sleeve 14 to deform as shown (FIG. 2). The engagement of the deployment suture 12 with the bottom side of sleeve 14, causes the middle of sleeve 14 to be pulled up, thereby causing more folding of anchor 10 and a better setting of anchor 10. The greater degree of engagement of deployment suture 12 with sleeve 14, causes a denser deployed anchor. If deployment suture 12 did not reenter sleeve 14 between the first terminus opening 26 and the second terminus opening 28, it would hang down into pilot hole 16, and not add to the transverse bulk of the deployed anchor 10, as shown in FIG. 3. Although this is not shown, anchor 10 digs into the sides of pilot hole 16.

In one embodiment, adapted to be anchored in a 2.9 mm pilot hole, sleeve 14 is made of braided polyester, is in a range of between 1 to 1.4 mm in diameter and is 28 mm long. The deployment suture 12 is a number 2 suture, having a 0.5 mm diameter, and is made of ultra-high molecular weight polyethylene (UHMWPE). Alternatively, deployment suture 12 is in the form of 1.4 mm width suture tape. In a further embodiment, sleeve 14 is made of a mix of polyester and UHMWPE. In a further embodiment, made for smaller diameter pilot holes, sleeve 14 is made entirely of braided fibers of UHMWPE. Further embodiments are adapted to anchor in pilot holes of 1.3 mm to 2.9 mm diameter. Further embodiments have 2 separate deployment strands 12, similarly engaged to sleeve 14. In one embodiment, both strands are USP #2 sutures, in another embodiment one deployment strand is a USP #2 suture and the other deployment strand is a suture tape, of depending on the variant, from 1.3 to 1.6 mm width. And in another embodiment the deployment strands are both suture tape, again depending on the variant, from 1.3 to 1.6 mm. In one embodiment, sleeve 14 is of a smaller than 1 mm diameter, such as a 0.6 mm diameter, to better fit into a smaller hole.

Referring to FIG. 4, in an alternative anchor embodiment 10', an additional suture length 30 is added, relative to anchor 10, to provide additional means for tying soft tissue to anchor 10, and thereby to bone. In further additional embodiments, additional suture lengths are added, in parallel to length 112, for additional options in tying tissue to bone.

The disclosed embodiments are illustrative, not restrictive. While specific configurations of the soft anchor have been described, it is understood that the present invention can be applied to a wide variety of medical technology. There are many alternative ways of implementing the invention.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A soft anchor, comprising:
   a) a sleeve, being a circular braided suture defining a lumen, and defining a first terminus, having a first terminus opening into said lumen and a second terminus having a second terminus opening into said lumen;
   b) a deployment suture, being of a smaller diameter than said sleeve, and wherein said deployment suture is engaged to said sleeve by extending into said lumen through a first broach point, then out of said sleeve through said first terminus opening, then into said sleeve through a second broach point, and then out of said lumen though a third broach point, then into said lumen through said second terminus opening and out of said sleeve though a fourth broach point, thereby creating a first lateral trap, between said first broach point and said first terminus opening, a second lateral trap, between said second terminus opening and said fourth broach point, and a central trap, between said second and third broach points.

2. The soft anchor of claim 1, wherein said deployment suture is made of ultra-high molecular weight polyethylene (UHMWPE).

3. The soft anchor of claim 1, wherein said deployment suture is a number 2 suture.

4. The soft anchor of claim 1, wherein said deployment suture is a suture tape having a width of 1.4 mm.

5. The soft anchor of claim 1, wherein said sleeve is made of braided polyester.

6. The soft anchor of claim 1, wherein said sleeve is braided from a mix of polyester and UHMWPE fibers.

7. The soft anchor of claim 1, wherein said sleeve is made of braided UHMWPE.

8. The soft anchor of claim 1, wherein said sleeve is 28 mm in length.

9. The soft anchor of claim 1, wherein said sleeve is between 1 and 1.4 mm in diameter.

10. The soft anchor of claim 1, wherein said sleeve is less than 1 mm in diameter.

11. The soft anchor of claim 1, further including an additional suture passing through said sleeve, thereby providing an additional two suture ends, which can be used to tie soft tissue.

12. A method of anchoring a suture to a pilot hole in bone, comprising:
   a) providing a soft anchor, including:
      i. a sleeve, being a circular braided suture defining a lumen, and defining a first terminus, having a first terminus opening into said lumen and a second terminus having a second terminus opening into said lumen;
      ii. a deployment suture, being of a smaller diameter than said sleeve, and wherein said deployment suture is engaged to said sleeve by extending into said lumen through a first broach point, then out of said sleeve through said first terminus opening, then into said sleeve through a second broach point, and then out of said lumen though a third broach point, then into said lumen through said second terminus opening and out of said sleeve though a fourth broach point, thereby creating a first lateral trap, between said first broach point and said first terminus opening, a second lateral trap, between said second terminus opening and said fourth broach point, and a central trap, between said second and third broach points;

b) providing an introducer tool sized to push said soft anchor into said pilot hole;
c) using said introducer tool to push said soft anchor into said pilot hole;
d) removing said introducer tool;
e) pulling on both ends of said deployment suture, and thereby causing said soft anchor to deform, expanding in a transverse dimension so that it is set in said pilot hole.

13. The method of claim 12, wherein said deployment suture is made of ultra-high molecular weight polyethylene (UHMWPE).

14. The method of claim 12, wherein said deployment suture is a number 2 suture.

15. The method of claim 12, wherein said deployment suture is a suture tape having a width of 1.4 mm.

16. The method of claim 12, wherein said sleeve is made of braided polyester.

17. The method of claim 12, wherein said sleeve is braided from a mix of polyester and UHMWPE fibers.

18. The method of claim 12, wherein said sleeve is made of braided UHMWPE.

19. The method of claim 12, wherein said pilot hole is 2.9 mm in diameter and said sleeve is in the range of 1 to 1.4 mm in diameter.

20. The method of claim 12, wherein said hole is less than 2 mm in diameter and said sleeve is less than 1 mm in diameter.

21. The method of claim 12, wherein pulling on both ends of said deployment suture causes said center trap to be pulled up.

22. The method of claim 12, wherein said soft anchor further includes an additional suture passing through said sleeve, thereby providing an additional two suture ends, which can be used to tie soft tissue.

* * * * *